US00PP23201P2

(12) United States Plant Patent
Kobayashi

(10) Patent No.: US PP23,201 P2
(45) Date of Patent: Nov. 20, 2012

(54) POINSETTIA PLANT NAMED 'PER1188'

(50) Latin Name: ***Euphorbia pulcherrima* Willd.**
Varietal Denomination: PER1188

(75) Inventor: Ruth Kobayashi, Carlsbad, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 28 days.

(21) Appl. No.: 13/065,258

(22) Filed: Mar. 17, 2011

(51) Int. Cl.
*A01H 5/00* (2006.01)

(52) U.S. Cl. ..... Plt./307; Plt./303

(58) Field of Classification Search ..... Plt./303, Plt./307
See application file for complete search history.

*Primary Examiner* — Susan McCormick Ewoldt
(74) *Attorney, Agent, or Firm* — C. A. Whealy

(57) ABSTRACT

A new and distinct cultivar of Poinsettia plant named 'PER1188', characterized by its compact, uniform, upright and mounded plant habit; vigorous growth habit; freely branching habit; dark green-colored leaves; early season flowering response; large inflorescences with bright red-colored flower bracts; and good post-production longevity.

1 Drawing Sheet

Botanical designation: *Euphorbia pulcherrima* Willd.
Cultivar denomination: 'PER1188'.

BACKGROUND OF THE INVENTION

The present invention relates to a new and distinct cultivar of Poinsettia plant, botanically known as *Euphorbia pulcherrima* Willd., and hereinafter referred to by the name 'PER1188'.

The new Poinsettia plant is a product of a planned breeding program conducted by the Inventor in Encinitas, Calif. The objective of the breeding program is to create new uniform Poinsettia plants having large inflorescences with bright red-colored flower bracts, early season flowering habit and excellent post-production longevity.

The new Poinsettia plant originated from a cross-pollination made by the Inventor in December, 2003 of a proprietary selection of *Euphorbia pulcherrima* Willd. identified as code number 1014, not patented, as the female, or seed, parent, with a proprietary selection of *Euphorbia pulcherrima* Willd. identified as code number PE2-16, not patented, as the male, or pollen, parent. The new Poinsettia plant was discovered and selected by the Inventor as a single flowering plant within the progeny of the stated cross-pollination in a controlled greenhouse environment in Encinitas, Calif. on Dec. 10, 2004.

Asexual reproduction of the new Poinsettia plant by terminal vegetative cuttings in a controlled greenhouse environment in Encinitas, Calif. since January, 2005 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environment such as temperature, daylength and light intensity, without, however, any variance in genotype.

The following traits have been repeatedly observed and are determined to be the unique characteristics of 'PER1188'. These characteristics in combination distinguish 'PER1188' as a new and distinct Poinsettia plant:

1. Compact, uniform, upright and mounded plant habit.
2. Vigorous growth habit.
3. Freely branching habit.
4. Dark green-colored leaves.
5. Early season flowering response; under natural season conditions, plants flower in early November in Southern California.
6. Large inflorescences with bright red-colored flower bracts.
7. Good post-production longevity.

In side-by-side comparisons conducted in Encinitas, Calif., plants of the new Poinsettia differ primarily from plants of the female parent in the following characteristics:

1. Plants of the new Poinsettia are more compact than plants of the female parent selection.
2. Plants of the new Poinsettia flower about two weeks earlier than plants of the female parent selection.
3. Flower bracts of plants of the new Poinsettia are bright red in color whereas flower bracts of plants of the female parent selection are dark red in color.

In side-by-side comparisons conducted in Encinitas, Calif., plants of the new Poinsettia differ primarily from plants of the male parent in the following characteristics:

1. Flower bracts of plants of the new Poinsettia are not as smooth as flower bracts of plants of the male parent selection.
2. Flower bracts of plants of the new Poinsettia are bright red in color whereas flower bracts of plants of the male parent selection are dark red in color.

Plants of the new Poinsettia can be compared to plants of the *Euphorbia pulcherrima* Willd. 'PER2804', disclosed in U.S. Plant Pat. No. 19,295. In side-by-side comparisons conducted in Encinitas, Calif., plants of the new Poinsettia differed primarily from plants of 'PER2804' in the following characteristics:

1. Plants of the new Poinsettia had darker green-colored leaves than plants of 'PER2804'.

2. Plants of the new Poinsettia flowered about five days later than plants of 'PER2804'.
3. Inflorescences of plants of the new Poinsettia had fewer cyathia than inflorescences of plants of 'PER2804'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1188' grown in a container.

The photograph at the top of the sheet is a close-up view of a typical inflorescence of 'PER1188'.

DETAILED BOTANICAL DESCRIPTION

Plants used in the aforementioned photographs and in the following description were grown during the winter in 16.5-cm containers in a polyethylene-covered greenhouse in Encinitas, Calif. and under natural season conditions and cultural practices which approximate those generally used in commercial Poinsettia production. During the production of the plants, day temperatures ranged from 20° C. to 27° C., night ranged from 15° C. to 20° C. and light levels ranged from 3,000 to 4,000 foot-candles. Measurements and numerical values represent averages for typical flowering plants. Plants were pinched one time and were 19 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1188'.

Parentage:

*Female, or seed, parent*.—Proprietary selection of *Euphorbia pulcherrima* Willd. identified as code number 1014, not patented.

*Male, or pollen, parent*.—Proprietary selection of *Euphorbia pulcherrima* Willd. identified as code number PE2-16, not patented.

Propagation:

*Type*.—Terminal vegetative cuttings.

*Time to initiate roots*.—About seven to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Compact, uniform, upright and mounded plant habit; inverted triangle; large inflorescences positioned above the foliar plane; vigorous growth habit.

*Plant height*.—About 27 cm.

*Plant diameter or spread*.—About 40 cm.

*Lateral branch description*.—Quantity: Freely branching habit, about seven lateral branches develop after pinching. Length: About 26 cm. Diameter: About 6 mm. Internode length: About 1.8 cm. Strength: Strong. Texture: Smooth, glabrous. Color: Close to 146B.

*Foliage description*.—Arrangement: Alternate, simple. Aspect: Flat. Length: About 12 cm. Width: About 9.4 cm. Shape: Ovate with shallow lobes. Apex: Acuminate. Base: Rounded. Margin: Entire with shallow lobes. Venation pattern: Pinnate, arcuate. Texture, upper surface: Sparsely pubescent. Texture, lower surface: Pubescent. Color: Developing leaves, upper surface: Close to N137C. Developing leaves, lower surface: Close to 147B. Fully expanded leaves, upper surface: Darker than N137A; venation, close to 146A. Fully expanded leaves, lower surface: Close to N137B; venation, close to 146C. Petiole: Length: About 6 cm. Diameter: About 3 mm. Texture, upper and lower surfaces: Smooth, glabrous. Color, upper surface: Close to 187C. Color, lower surface: Close to 183B.

Inflorescence description:

*Inflorescence type and habit*.—Inflorescences are compound corymbs of cyathia with colored flower bracts subtending the cyathia; inflorescences positioned above the foliar plane.

*Quantity of inflorescence*.—One inflorescence develops per lateral branch.

*Fragrance*.—Not detected.

*Flowering response*.—Early season flowering response; under natural season conditions, plants typically flower on November 7$^{th}$ in Southern California; under artificial long nyctoperiod/short photoperiod conditions, plants flower about 6.5 weeks later.

*Post-production longevity*.—Good post-production longevity; plants of the new Poinsettia maintain good substance and flower bract color for about four weeks under interior conditions; inflorescences persistent.

*Inflorescence size*.—Diameter: About 26 cm. Height (depth): About 11 cm.

*Flower bracts*.—Quantity per inflorescence: About 18. Length, largest bracts: About 12.5 cm. Width, largest bracts: About 11 cm. Shape: Ovate. Apex: Acuminate. Base: Rounded. Margin: Entire. Texture, upper and lower surfaces: Somewhat rugose, glabrous. Aspect: Initially angling upwardly and becoming closer to horizontal with development. Venation pattern: Pinnate, arcuate. Color: Developing or transitional bracts, upper surface: Close to 53B. Developing or transitional bracts, lower surface: Close to 184C. Fully expanded bracts, upper surface: Close to 46A; venation, close to 46A; color becoming closer to 53B with development. Fully expanded bracts, lower surface: Close to 53B; venation, close to 53B. Bract petiole: Length: About 4.5 cm. Diameter: About 2.5 mm. Texture, upper and lower surfaces: Smooth, glabrous. Color, upper and lower surfaces: Close to 187C.

*Cyathia*.—Quantity per corymb: About 15. Length: About 1 cm. Width: About 6 mm. Shape: Ovoid. Color, immature and mature: Close to 146C.

*Nectaries*.—Quantity per cyathium: One. Length: About 5 mm. Width: About 3 mm. Shape: Elliptical to ovoid. Color: Close to N25A to N25B.

*Peduncles*.—Length: About 5 mm. Diameter: About 3 mm. Strength: Strong. Aspect: Mostly upright to slightly outwardly. Texture: Smooth, glabrous. Color: Close to 146D.

*Reproductive organs*.—Stamens: Quantity per cyathium: About 10 to 15. Filament length: About 2 mm. Filament color: Close to 187D. Anther shape: Oval; bi-lobed. Anther length: About 1 mm. Anther color: Close to 182B. Amount of pollen: Scarce. Pollen color: Close to 14B. Pistils: Plants of the new Poinsettia have not been observed to develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 35° C.

It is claimed:

1. A new and distinct Poinsettia plant named 'PER1188' as illustrated and described.

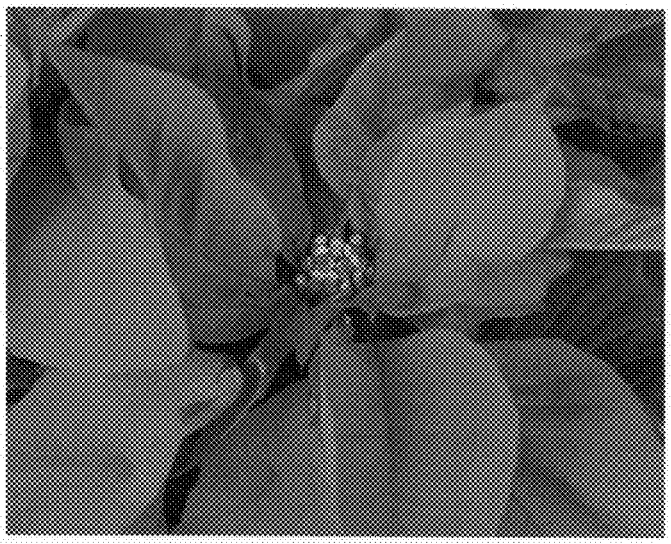
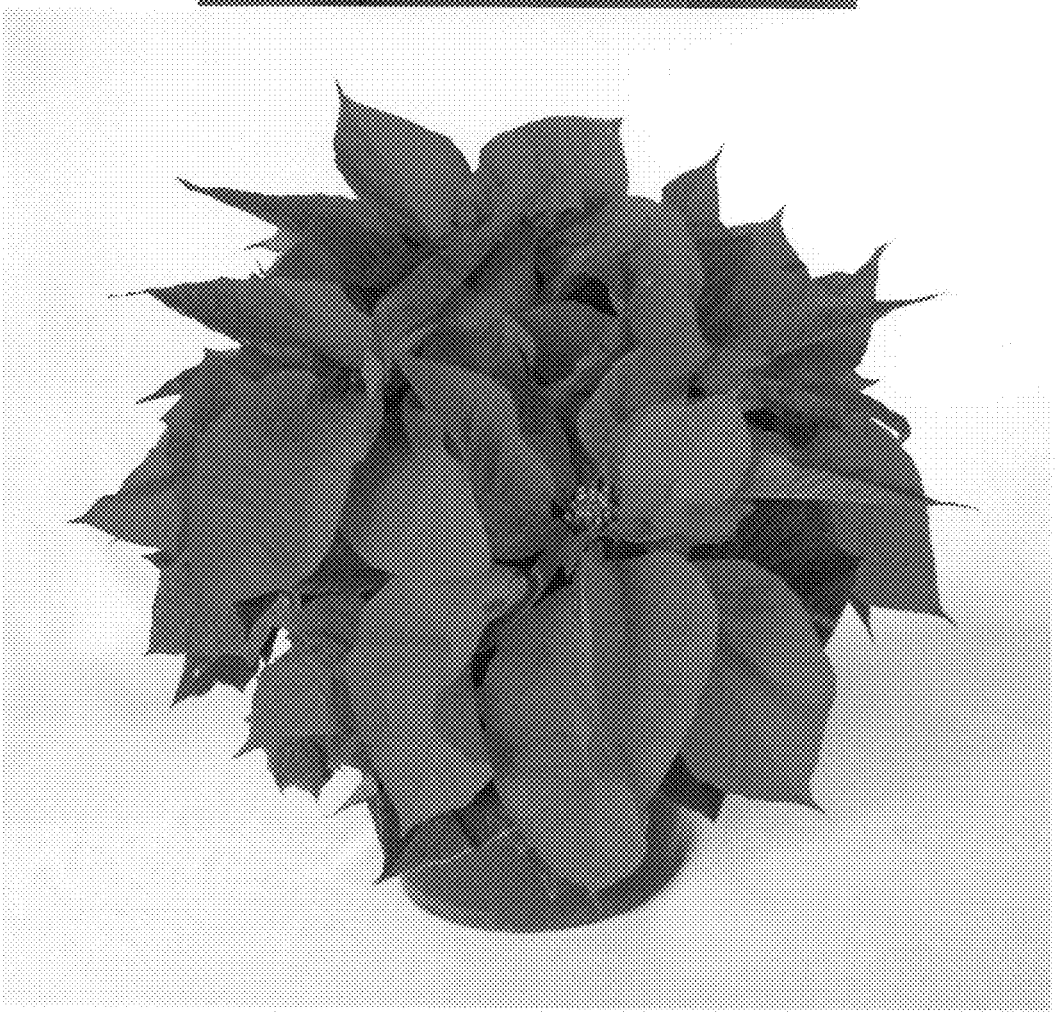

* * * * *